United States Patent
Mitchell (10) Patent No.: US 8,756,974 B2
(45) Date of Patent: Jun. 24, 2014

(54) MOUTH ALCOHOL TESTER

(75) Inventor: John Mitchell, Manchester, MO (US)

(73) Assignee: Alcotek, Inc., St. Louis, MO (US)

( * ) Notice: Subject to any disclaimer, the term of this patent is extended or adjusted under 35 U.S.C. 154(b) by 0 days.

(21) Appl. No.: 13/427,505

(22) Filed: Mar. 22, 2012

(65) Prior Publication Data

US 2012/0174651 A1 Jul. 12, 2012

Related U.S. Application Data (63) Continuation of application No. 12/168,781, filed on Jul. 7, 2008, now Pat. No. 8,161,793.

(60) Provisional application No. 60/948,125, filed on Jul. 5, 2007.

(51) Int. Cl.
*G01N 33/497* (2006.01)

(52) U.S. Cl.
USPC ............................................. 73/23.3; 422/84

(58) Field of Classification Search
USPC ............................................. 73/23.3; 422/84
See application file for complete search history.

(56) References Cited

U.S. PATENT DOCUMENTS

| | | | |
|---|---|---|---|
| 4,297,871 A * | 11/1981 | Wright et al. | 73/23.3 |
| 4,300,384 A | 11/1981 | Wiesner et al. | |
| 4,749,553 A | 6/1988 | Lopez et al. | |
| 4,868,545 A * | 9/1989 | Jones | 340/573.1 |
| 5,291,898 A | 3/1994 | Wolf | |
| 5,303,575 A | 4/1994 | Brown et al. | |
| 5,376,555 A | 12/1994 | Forrester et al. | |
| 5,458,853 A * | 10/1995 | Porter et al. | 422/84 |
| 5,929,319 A | 7/1999 | King et al. | |
| 6,123,828 A | 9/2000 | Williams et al. | |
| 6,582,376 B2 * | 6/2003 | Baghdassarian | 600/543 |
| 6,811,751 B1 * | 11/2004 | Olsson et al. | 422/84 |
| 6,837,987 B1 | 1/2005 | King | |
| 6,853,956 B2 * | 2/2005 | Ballard et al. | 702/183 |
| 6,923,040 B2 | 8/2005 | Stock | |
| 6,967,581 B2 | 11/2005 | Karsten | |

(Continued)

FOREIGN PATENT DOCUMENTS

| | | |
|---|---|---|
| DE | 4443142 A1 * | 6/1996 |
| DE | 4443142 C2 * | 10/1998 |

(Continued)

OTHER PUBLICATIONS

"Dart Sensors Ltd," http://www.dart-sensors.com/pages/alcohol.php, printed on Jul. 11, 2008, pp. 1-2.

(Continued)

*Primary Examiner* — Lisa Caputo
*Assistant Examiner* — Punam Roy
(74) *Attorney, Agent, or Firm* — Lewis, Rice & Fingersh, L.C.

(57) ABSTRACT

This application discloses a system for detecting mouth alcohol which is integrated with a breath-measuring instrument. In an embodiment, the breath-measuring instrument comprises a single fuel cell system, wherein the single fuel cell measures an individual's alveolar breath as well as detection of any mouth alcohol. In a further embodiment, the breath-measuring instrument comprises a first fuel cell and a second fuel cell, wherein the first fuel cell measures alveolar breath and the second fuel cell detects mouth alcohol.

16 Claims, 8 Drawing Sheets

(56) References Cited

U.S. PATENT DOCUMENTS

| | | | |
|---|---|---|---|
| 7,122,154 B1 | 10/2006 | Forrester et al. | |
| 7,749,169 B2* | 7/2010 | Bayer et al. | 600/532 |
| 7,779,840 B2* | 8/2010 | Acker et al. | 128/204.16 |
| 8,176,766 B1* | 5/2012 | Ruiz et al. | 73/23.3 |
| 2007/0093725 A1* | 4/2007 | Shaw | 600/543 |
| 2007/0154765 A1 | 7/2007 | Bayer et al. | |
| 2008/0284418 A1 | 11/2008 | Lueck | |
| 2009/0007634 A1 | 1/2009 | Mitchell | |
| 2009/0087920 A1* | 4/2009 | Pettersson et al. | 436/132 |

FOREIGN PATENT DOCUMENTS

| | | | |
|---|---|---|---|
| GB | 2295679 A | * | 6/1996 |
| KR | 1998081942 A | | 11/1998 |
| KR | 100448728 B1 | | 11/2004 |
| KR | 100478280 B1 | | 8/2005 |
| WO | 2005029619 A1 | | 3/2005 |
| WO | 2006120409 A2 | | 11/2006 |

OTHER PUBLICATIONS

"Blood alcohol content," http://en.wikipedia.org/wiki/Blood_alcohol_content, printed on Jun. 19, 2008, pp. 1-9.

"Alcoholic beverage," http://en.wikipedia.org/wiki/Alcoholic_beverage, printed on Jun. 19, 2008, pp. 1-17.

"Short-term effects of alcohol," http://en.wikipedia.org/wiki/Short-term_effects_of_alcohol, printed on Jun. 19, 2008, pp. 1-9.

"History of alcohol," http://en.wikipedia.org/wiki/History_of_alcohol, printed on Jun. 19, 2008, pp. 1-9.

"Breathalyzer," http://en.wikipedia.org/wiki/Breathalyzer, printed on Jun. 19, 2008, pp. 1-9.

International Search Report, International Patent Application No. PCT/US08/69360, mailed on Jan. 21, 2009, 13 pages.

* cited by examiner

MOUTH ALCOHOL TESTER

CROSS REFERENCE TO RELATED APPLICATIONS

This application is a Continuation of U.S. patent application Ser. No. 12/168,781, filed Jul. 7, 2008 now U.S. Pat. No. 8,161,793 and currently, which in turn claims benefit of U.S. Provisional Application No. 60/948,125, filed Jul. 5, 2007. The entire disclosure of all the above documents is incorporated herein by reference.

BACKGROUND OF THE INVENTION

1. Field of the Invention

The present invention generally relates to the field of breath alcohol detection systems. In particular, to fuel cell breath alcohol detection systems that have the ability to detect the presence of mouth alcohol.

2. Description of Related Art

An alcoholic beverage is a drink containing ethanol, commonly known as alcohol, although in chemistry the definition of alcohol includes many other compounds. Alcohol, specifically ethanol, is a psychoactive drug and is a powerful central nervous system depressant with a range of side effects.

Alcohol has a biphasic effect on the body, which is to say that its effects change over time. In the initial stages of intoxication, alcohol generally produces feelings of relaxation and cheerfulness. Further consumption however affects the brain leading to slurred speech, blurred vision, clumsiness and delayed reflexes, among other coordination problems. This condition is commonly referred to as intoxication or drunkenness, and eventually subsides when the alcohol has fully metabolized in the body.

When a human drinks alcohol, the alcohol housed in the stomach passes into the bloodstream. Cell membranes are highly permeable to alcohol, so once alcohol is in the bloodstream it can diffuse into nearly every biological tissue of the body. Once in the bloodstream, the alcohol circulates to the brain, resulting in intoxication, loss of inhibition and impairment of motor skills such as driving a vehicle. The amount of alcohol consumed and the circumstances surrounding consumption play a large role in determining the extent of an individual's intoxication. Examples of such circumstances include the amount of food in the stomach at the time of alcohol consumption and the hydration level of the individual at the time of consumption, among others.

Due to the coordination impairment and other symptoms associated with intoxication and drunkenness, most countries have laws against drunk driving, i.e., driving with a certain concentration of ethanol in the blood. The legal threshold of blood alcohol content ranges from 0.0% to 0.08%, depending on the jurisdiction. Punishments for operating a vehicle over the legal limit in a given jurisdiction generally include fines, temporary loss of an individual's driving license and imprisonment. Creation of these laws has led to a market for devices to accurately measure the blood alcohol content of individuals operating motor vehicles.

Blood alcohol content (BAC) or blood alcohol concentration is the concentration of alcohol in the blood (weight per unit volume). While blood alcohol content can be directly measured in a hospital laboratory setting, it is more common for it to be measured in law enforcement situations by estimation from an individual's breath alcohol concentration using a breath alcohol testing machine.

Breath Alcohol Concentration (BrAC) is commonly measured in grams of alcohol per 210 Liters of breath (g/210 L) or milligrams of alcohol per Liter of breath (mg/L). However, there are other units of measure as well used by those skilled in the art.

Breath alcohol testers assume that the individual being tested is average in various ways. For example, on average the ratio of BAC to breath alcohol content (the partition ratio) is 2100 to 1. In other words, there are 2100 parts of alcohol in the blood for every part in the breath in an equal volume. The actual ratio can vary from person to person and moment to moment. However, it is generally accepted that a partition ration of 2100:1 underestimates the actual blood alcohol concentration of individuals, i.e., is in favor of the subject in a legal sense.

For purposes of law enforcement, most jurisdictions don't concern themselves with the exact amount of impairment due to drinking Rather, they follow the so-called "per se" laws by which an individual's measured BAC or BrAC level is the primary method used to define intoxication and provides a rough measure of an individual's impairment. Although the degree of impairment varies among individuals with the same BAC, since BAC or BrAC are objective measurements they are therefore legally useful and difficult to contest in court.

In the field of breath alcohol testing, it is well known that if a breath measuring instrument analyzes an alveolar (deep lung) sample of breath, the concentration of alcohol in that sample is a reliable indicator of a human subject's intoxication level. This is because the alveolar breath is in equilibrium with the blood due to the intimate communication between blood and breath in the lung, between capillaries and alveoli.

Generally, when an alcohol breath test is made, the subject is required to blow into a measuring instrument. Instruments use various sensors to determine when alveolar breath is delivered (as opposed to upper respiratory breath from the mouth or throat) so that an accurate measurement of deep lung air may be made. Those skilled in the art realize such methods might include measurements of flow, volume, time, pressure, or real-time breath alcohol concentration profiling.

Making a measurement before alveolar air has migrated from the lungs to the instrument during a blow will typically result in a low reading. This is because breath from the upper respiratory tract generally has a lower concentration of alcohol than deep lung air.

There is a condition where the breath generated from the upper respiratory tract has a higher concentration of alcohol than deep lung air. This is generally known as "mouth alcohol" and is typically the result of an alcoholic drink within the 15 minutes previous to the tested breath sample. This condition can cause a falsely high breath alcohol tester reading since the reading is not a pure sample of alveolar breath. By definition, mouth alcohol was not absorbed through the stomach and intestines and passed through the blood to the lungs. As stated previously, in analyzing a subject's breath sample, a breath alcohol tester is making an assumption that the alcohol in the breath sample came from alveolar air, i.e., air exhaled from deep within the lungs. However, alcohol from the mouth, throat or stomach may have contributed to the reading under certain conditions.

With virtually any current alcohol breath tester, one can easily prove the existence of mouth alcohol and its distorting effect on measured alcohol concentration. This is most easily observed when a subject is sober. Table 1 below provides data from an experiment meant to illustrate mouth alcohol's presence and effect. Subjects of such an experiment are not intoxicated. However, current fuel cell alcohol breath testers do not take into account the presence of mouth alcohol. In recognition of mouth alcohol's distorting effects on an alcohol breath tester's results, certified breath operators are trained to carefully observe a test subject for at least 15-20 minutes before administering the test to insure nothing is placed into the individual's mouth as a way to help guard against mouth alcohol contamination.

TABLE 1

| Time (mm:ss) | Action | Result (g/210 L) | Comment |
| --- | --- | --- | --- |
| 0:00 | Blow | 0.000 | Sober Subject |
| 0:30 | — | — | Swish ½ ounce of vodka in the mouth for 15 seconds. Spit vodka out; don't swallow. |
| 1:50 | Blow | 0.352 | Maximum reading on many breath testers is 0.400 g/210 L. This level may be lethal. |
| 4:50 | Blow | 0.101 | In many U.S. states, this reading is over the legal driving limit of 0.080 g/210 L. |
| 6:00 | Blow | 0.059 | In some European countries, this level will result in loss of license. |
| 7:10 | Blow | 0.040 | In many workplaces, this reading and above would result in termination. |
| 8:45 | Blow | 0.020 | In many workplaces, this reading and above would result in disciplinary action. |
| 10:00 | Blow | 0.011 | In some jurisdictions, juveniles at this level will lose their driving license. |
| 11:15 | Blow | 0.008 | — |
| 12:30 | Blow | 0.006 | Many breath testers don't even read this low. |
| 14:00 | Blow | 0.004 | — |
| 15:30 | Blow | 0.000 | 15 minutes has expired since alcohol was introduced into the mouth. |

To combat the problems of mouth alcohols, traditionally, in law enforcement, an officer will observe the subject for fifteen minutes prior to a breath test so that the officer may be able to testify in court that the subject did not put anything in the mouth, including alcohol, at anytime during the fifteen minutes prior to submitting a breath sample for measurement. In addition, the jurisdiction will typically require that two tests be taken on the subject separated by some number of minutes. The two tests must agree within a certain range or else the test is not valid. If the two tests agree, this gives further weight to evidence that no mouth alcohol is present.

However, since the problems of falsely higher tester readings due to mouth alcohol have become more widely known, manufacturers of breath alcohol test equipment have developed a variety of techniques to detect a mouth alcohol condition during a subject blow and report to the operator that a valid alcohol breath test is not possible at this time. Current known systems of mouth alcohol detection are all based on infrared absorption measurement systems and are known to those skilled in the art. These systems monitor the breath alcohol concentration of the blow from the beginning to end and look for distinctive profiles of breath alcohol concentration over time to determine whether there is a mouth alcohol condition. Those skilled in the art realize that these infrared detection systems might vary in their ability to detect all mouth alcohol conditions depending on the characteristics of the specific system used, those characteristics being as follows:

Signal-to-noise ratio.
Signal stability under varying ambient conditions.
Degradation of the measurement chamber components over time.
Deadspace of the system.
Specific detection algorithms.

Because of their added benefit of credibility, buyers of breath alcohol testers used in law enforcement often require mouth alcohol detection systems. These systems are most often used in conjunction with a 15 minute observation period to give further weight to evidence provided by the breath tester. Further, most jurisdictions require two consecutive breath tests on a subject. These two tests are typically spread over a small time period and must agree within a certain tolerance, such as 0.020 g/210 L. If the two tests do not agree, this may also be a sign of a mouth alcohol condition. Many buyers have also developed evaluation test regimens to determine the effectiveness of a given mouth alcohol detection system.

Some jurisdictions are now performing evidential breath tests on the roadside at the time of arrest. A test taken roadside is always closer to the subject's active drinking time than if the subject were driven to a station before testing. This makes mouth alcohol detection even more of a concern than in the past.

In summary, current alcohol testers in law enforcement have developed a three-legged approach to ensure that a breath test result is a true indication of a subject's BAC, showing no effects of a mouth alcohol condition:

1. A fifteen minute observation period of the subject before testing.
2. Two consecutive tests on a subject separated by a small time period that must agree within a certain tolerance.
3. Mouth alcohol detection by the breath-measuring instrument.

A variety of techniques are currently available to detect a mouth alcohol condition during a subject blow and report to the operator that a valid alcohol breath test is not possible at that time. As stated previously, current known systems of mouth alcohol detection are based on infrared absorption measurement systems. Many infrared-based breath testers consist of a measuring chamber that a subject's breath passes through continuously during a blow. In its simplest form, a detector across the sample chamber from an infrared source can measure the amount of infrared energy absorbed by the alcohol molecules in the breath in between. The higher the concentration of alcohol, the more energy is absorbed. This forms the basis of an instrument that can measure and report accurate alveolar breath alcohol concentrations.

A principal advantage of infrared is that it is a real-time continuous measuring system that can profile the alcohol concentration of a subject blow from beginning to end. Algorithms can then analyze this profile of concentration versus time and notify the operator when there are indications of mouth alcohol.

Figure 1:
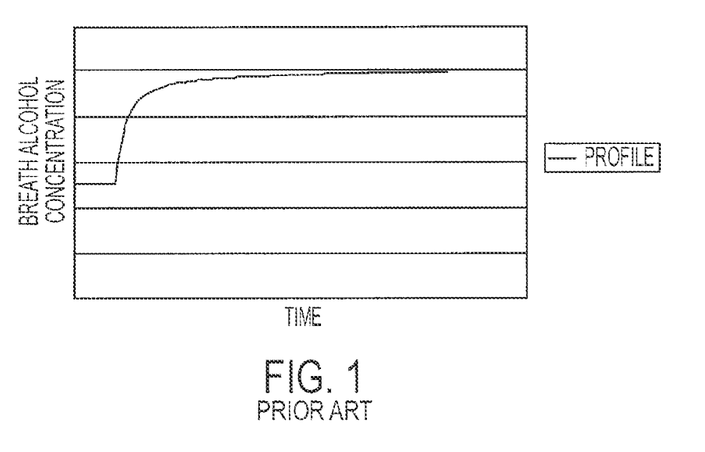
FIG. 1 shows an exemplary concentration profile without mouth alcohol conditions as known in the art.

An infrared breath profile of a drunken subject, without the subject having mouth alcohol, taken with current technology is exemplified in FIG. 1. At the beginning of the blow, as the lower concentration upper respiratory tract empties, the concentration begins to climb as deeper and deeper lung air begins to empty into the instrument. As the lungs approach the end of exhalation, the concentration reaches a plateau, indicating that deep lung alveolar breath is being measured. The plateau level is considered the measurement for that blow.

Figure 2:
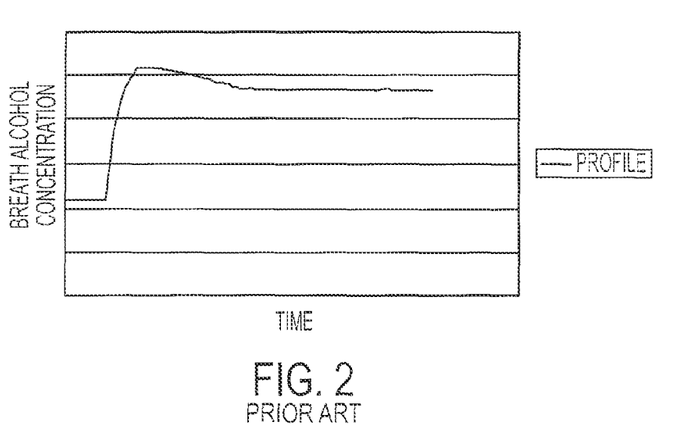
FIG. 2 shows an exemplary concentration profile with mouth alcohol conditions as known in the art.

When a subject blows similarly, but with a mouth alcohol condition, the early concentration profile from the upper respiratory tract can actually be higher than the alveolar concentration. Without mouth alcohol detection algorithms, this could result in an incorrect reading on the subject, or the inability to make a reading at all. A typical such curve is indicated in FIG. 2 and could typically be detected by an infrared-based mouth alcohol detector.

Another current type of breath alcohol tester is the fuel cell breath tester. Typically, current fuel cell sensors do not perform a continuous real-time analysis of a breath exhalation like the infrared systems. Fuel cell systems typically use other means to determine when deep-lung air is present in the measuring chamber, by monitoring characteristics of the subject blow such as flow, volume, time, and pressure, along with certain algorithms known to those skilled in the art. When the system has determined that alveolar air is present, a small fixed volume of breath is taken into an electrochemical fuel cell. The alcohol is burned in the fuel cell and a certain number of electrons are produced for each molecule of alcohol burned. These electrons are counted by an external circuit and a measurement is produced. By always taking a fixed volume sample, the test is standardized; when the breath sample contains twice the concentration of alcohol compared to another sample, twice the electrons are produced and the measurement is twice as large.

A principal advantage of fuel cell systems over infrared systems is lower procurement and maintenance costs. Even with adding sensors for flow, volume, time, or pressure, the fuel cell based system can be made at much lower cost. The drawback of current fuel cell systems compared to infrared is the lack of a real-time, continuous measurement system; i.e. the instrument itself does not have the ability to detect mouth alcohol. To compensate, many fuel cell users still incorporate the two legs of a mouth alcohol system, i.e., a fifteen minute wait, and the two subject tests mentioned above. However, they lack the third leg, i.e., an instrument-based detection system.

Some systems have attempted to combine the advantages of both systems and include instruments that contain dual analysis systems, i.e., infrared and fuel cell. This is meant to offer a system that overcomes the disadvantages of each type, but becomes costly. Other dual technology has used a lower-cost infrared system just for mouth alcohol detection and used the fuel cell only for the measurement of final result. However, this system also suffers a cost disadvantage compared to a strictly fuel cell based system.

SUMMARY OF THE INVENTION

The following is a summary of the invention in order to provide a basic understanding of some of the aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, disclosed herein, among other things, is an apparatus for detecting mouth alcohol which is integrated with a breath-measuring instrument. In an embodiment, the breath-measuring instrument comprises a single fuel cell system, wherein the single fuel cell measures an individual's alveolar breath as well as detection of any mouth alcohol. In a further embodiment, the breath-measuring instrument comprises a first fuel cell and a second fuel cell, wherein the first fuel cell measures alveolar breath and the second fuel cell detects mouth alcohol. In further embodiments, the second fuel cell could be separate from the first.

There is described herein, among other things, a breath alcohol tester, comprising: a breath manifold; a flow restriction; and a fuel cell; such that the breath manifold is designed to accept breath from a human subject, the breath including an early breath followed by a later breath; the action of the breath in the breath manifold against the flow restriction creates a positive pressure; the positive pressure forces at least a portion of the early breath into the fuel cell; the amount of alcohol in the early breath is calculated by the fuel cell as a first value; at least a portion of the later breath is drawn into the fuel cell; the amount of alcohol in the later breath is calculated by the fuel cell as a second value; the ratio of the first value to the second value is determined and compared to a predetermined threshold; and if the ratio exceeds the threshold, the breath alcohol tester indicates the presence of mouth alcohol.

In an embodiment of the breath alcohol tester, the portion of the early breath has a smaller volume than the portion of the later breath.

In an embodiment of the breath alcohol tester, the threshold is between about 0.05 and 0.07.

In an embodiment of the breath alcohol tester, the threshold is about 0.06.

In an embodiment of the breath alcohol tester, the tester includes a second fuel cell, the second fuel cell also taking in at least a portion of the later breath.

In an embodiment of the breath alcohol tester, the second fuel cell indicates the human subject's breath alcohol level in the event that the breath alcohol tester does not indicate the presence of mouth alcohol.

In an embodiment of the breath alcohol tester the portion of said early breath comprises a plurality of samples taken over time, a continuous sample taken up until the later breath, or an integrated sample.

In an embodiment of the breath alcohol tester, the later breath comprises alveolar breath.

In an embodiment of the breath alcohol tester, the later breath comprises alveolar breath.

In an embodiment of the breath alcohol tester, the breath manifold is used to distinguish the early breath from the later breath.

In an embodiment of the breath alcohol tester, the pressure is used to monitor flow of breath.

Also described herein is a breath alcohol tester, comprising: a breath manifold; a flow restriction; a first fuel cell; and a second fuel cell; in which the breath manifold is designed to accept breath from a human subject, the breath including an early breath followed by a later breath; the action of the breath in the breath manifold against the flow restriction creates a positive pressure; the positive pressure forces at least a portion of the early breath into the first fuel cell; the amount of alcohol in the early breath is calculated by the first fuel cell as a first value; at least a portion of the later breath is drawn into the second fuel cell; the amount of alcohol in the later breath is calculated by the second fuel cell as a second value; the ratio of the first value to the second value is determined and compared to a predetermined threshold; and if the ratio exceeds the threshold, the breath alcohol tester indicates the presence of mouth alcohol.

An embodiment of the dual fuel cell breath alcohol tester in which a portion of the early breath has a smaller volume than the portion of the later breath.

An embodiment of the dual fuel cell breath alcohol tester in which the threshold is between about 0.05 and 0.07.

An embodiment of the dual fuel cell breath alcohol tester in which the threshold is about 0.06.

An embodiment of the dual fuel cell breath alcohol tester in which the later breath comprises alveolar breath.

An embodiment of the dual fuel cell breath alcohol tester in which the pressure within the breath manifold is used to distinguish the early breath from the later breath.

An embodiment of the dual fuel cell breath alcohol tester in which the pressure is used to monitor flow of breath.

Also described herein is a method for detecting the presence of mouth alcohol, the method comprising: having a human subject breath into a breath manifold of a breath tester, the breath of the human subject including an early breath followed by a later breath; having at least a portion of the early breath enter into a fuel cell; determining an amount of alcohol in the early breath at the fuel cell; having at least a portion of the later breath enter into the fuel cell; determining an amount of alcohol in the later breath at the fuel cell; calculating the ratio of the amount of alcohol in the early breath to the amount of alcohol in the later breath; comparing the ratio to a predetermined threshold; and if the ratio exceeds the threshold, indicating the presence of mouth alcohol.

An embodiment of the method in which the threshold is between about 0.05 and 0.07.

An embodiment of the method in which the threshold is about 0.06.

DETAILED DESCRIPTION OF PREFERRED EMBODIMENT(S)

The following detailed description illustrates the invention by way of example and not by way of limitation.

Figure 3:
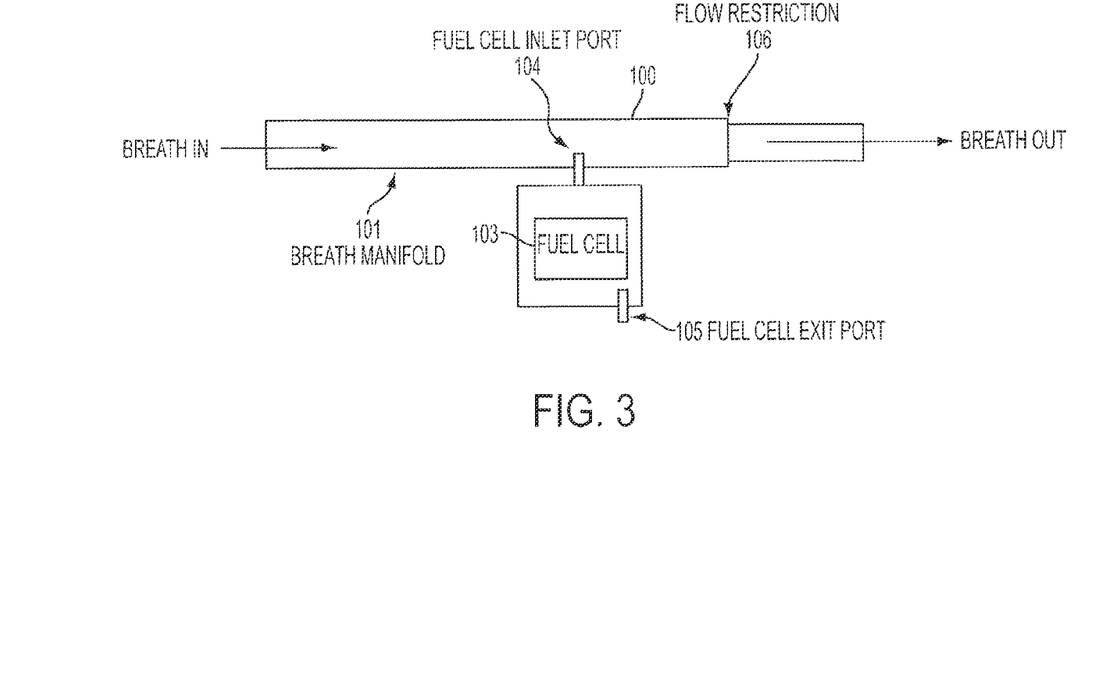
FIG. 3 shows a view of an embodiment of a single fuel cell system.

FIG. 3 shows an embodiment of a single fuel cell system (100) that detects mouth alcohol. Those skilled in the art would recognize that while blowing through a breath manifold (101) against a flow restriction (106), positive pressure would develop in the manifold (101) compared to ambient pressure or initial pressure in the fuel cell (103) due to space constraints inside the manifold (101) as pressing into the flow restriction (106). This back pressure in the manifold (101) serves to force a small amount of the early breath sample into the fuel cell (103), giving the desired mouth alcohol sample, i.e., a first measuring sample that precedes the alveolar breath sample. The manifold (101) could be a permanent part of the alcohol breath tester or it could be a disposable manifold often referred to as a disposable mouthpiece.

Figure 8:
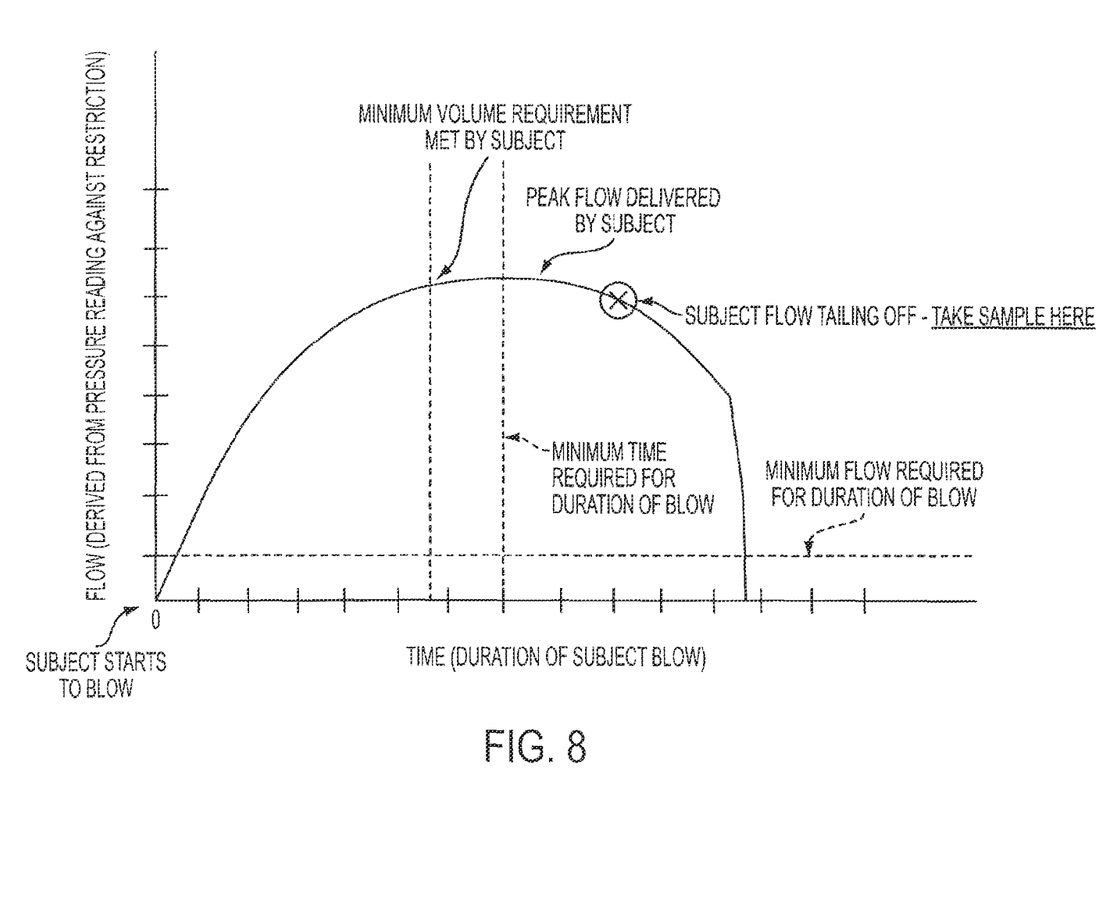
FIG. 8 shows data from an exemplary introduction of breath into a fuel cell system in which the manifold pressure is used as an indication of flow, which along with time, is used to monitor volume and flow to determine when a blowing subject has reached the accurate end-of-breath stage.

In an embodiment, measuring the pressure inside the manifold (101) during a subject blow can be used as an indication of flow, which, along with time, could be used to monitor volume and flow to determine when a blowing subject has reached the accurate end-of-breath stage, i.e., the individual's alveolar breath. One example of how this is done is shown in FIG. 8. At the indicated sampling time, a sampling system (not shown) may be used to draw the main, fixed volume alveolar breath sample into the fuel cell (103) for analysis, i.e., the second measuring sample. Typically, this sampling system is some sort of electromechanical volume-displacement device such as a pump, piston, or diaphragm. The mechanism will displace a fixed volume of subject breath sample from the manifold into a chamber external to the manifold that is in communication with the fuel cell. This happens nearly instantaneously. Once this discreet sample is taken, any alcohol in the sample reacts with the fuel cell in an expected manner and the alveolar breath reading is derived therefrom.

In order to employ a single fuel cell (103) to measure both the subject's alveolar breath and to detect the presence of mouth alcohol, there will generally be a mechanism, a second method in addition to the volume-displacement method mentioned above, for introducing a mouth alcohol sample into the cell (103) prior to the typical alveolar breath sample. Because a mouth alcohol condition presents an elevated breath alcohol concentration at the beginning of the subject's blow, this sample is preferably introduced into the fuel cell (103) beginning with the start of the blow and continuing until the alveolar sample is taken. So as not to influence the accuracy of the alveolar reading, the magnitude of the early, possibly mouth alcohol, reading should be much smaller, i.e., on a typical non mouth alcohol reading, the number of alcohol molecules exposed to the fuel cell should be much less than the number exposed at the alveolar sample.

Figure 5:
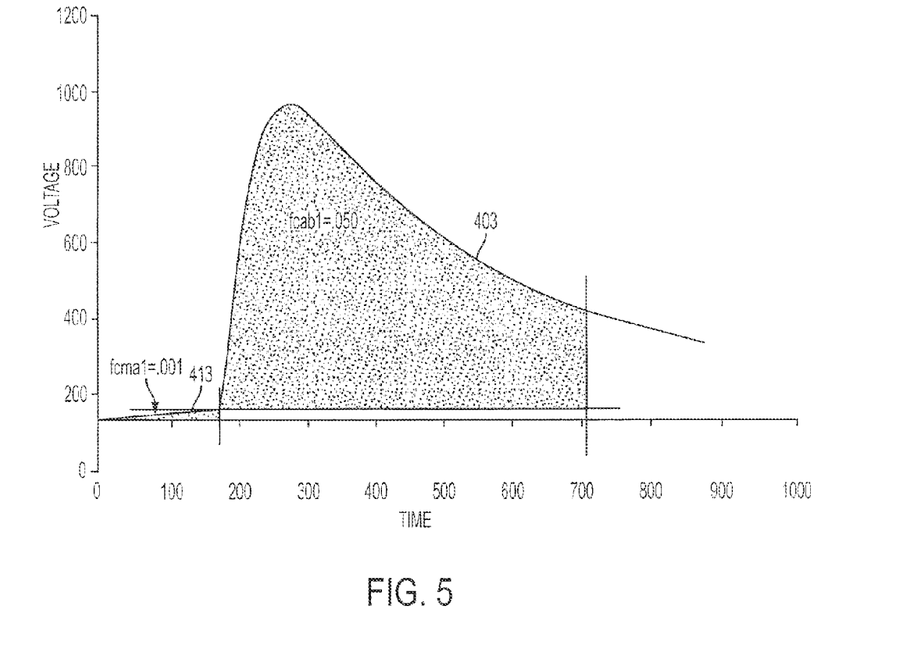
FIG. 5 shows data from an exemplary introduction of alcohol into an embodiment of a fuel cell during a valid, non-mouth-alcohol breath sample.
Figure 6:
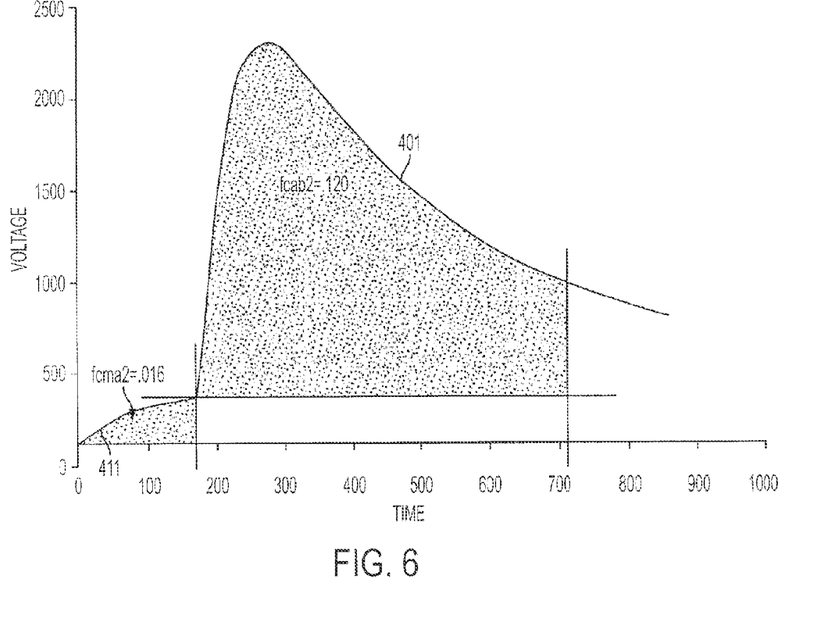
FIG. 6 shows data from an exemplary introduction of alcohol into an embodiment of a fuel cell during a breath sample with a mouth alcohol condition.

The amount of alcohol burned by the cell (103) during the blow, prior to taking the alveolar sample, may then be measured in an embodiment; that measurement may be labeled fcma as shown in FIGS. 5 and 6. Note that the calculation of fcma may or may not use the same method that will be employed to measure the alveolar sample; however, like the alveolar measurement, the fcma calculation will be a function of the signal returned from electronics (not shown) or other means for analyzing and returning the fuel cell (103) output.

Once the subject's end-of-breath has been reached, as seen in FIG. 8, the alveolar sample may be taken into the fuel cell (103). The amount of alcohol burned by the cell (103) as a result of this discreet sample may then be measured and analyzed according to methods known in the art; that measurement may be labeled fcab. In order to detect mouth alcohol, the ratio of fcma-to-fcab is compared to a predetermined threshold that may be called thma; if the ratio exceeds this threshold, the operator of the device is notified that the alveolar sample is invalid and mouth alcohol should be reported.

Figure 4:
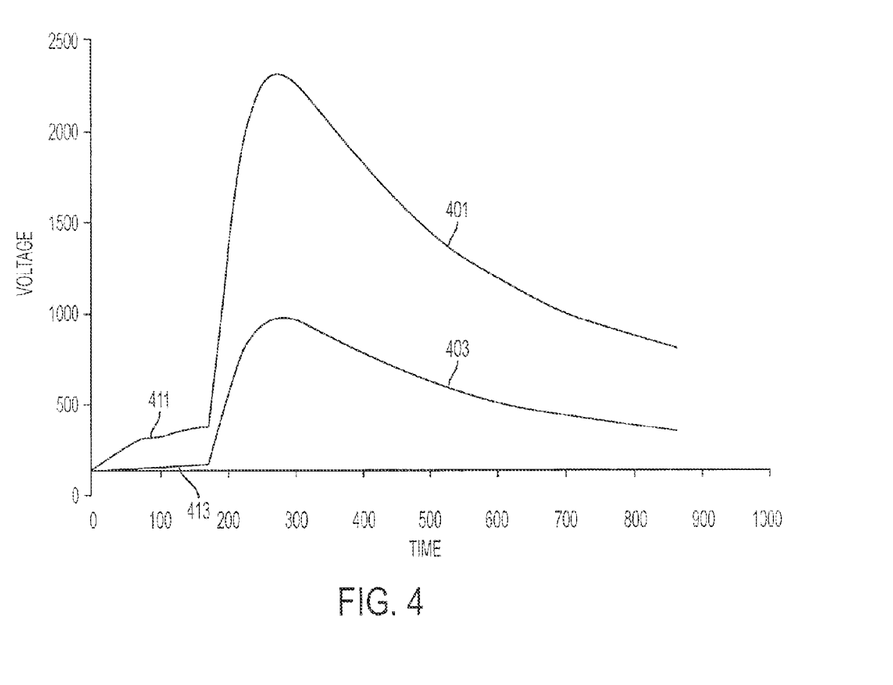
FIG. 4 shows data from an exemplary introduction of alcohol into an embodiment of a fuel cell with and without a mouth alcohol condition.

FIG. 4 provides an example of the described calculation. The larger curve (401) is representative of a mouth alcohol condition; the smaller curve (403) is not and correctly represents BAC. At approximately 175 on the time axis, both curves start to steeply rise. This is the point where the fixed volume sample of alveolar breath was taken into the fuel cell (103). Before this time, the low rise portion (411) and (413) of the curves (401) and (403) represents the initial mouth alcohol sample introduced into the fuel cell (103) during the blow before deep lung air is sampled.

FIG. 5 provides an enlarged view of the curve (403) in FIG. 4. It shows the filtered output of a fuel cell (103) during an exemplary valid, non-mouth-alcohol breath sample. The small response to the initial pre-sample alcohol introduced during the blow in this exemplary sample results in a fcma result of about 0.001 g/210 L. In the example in FIG. 5, the subject has a moderate breath alcohol concentration of about 0.050 g/210 L, which will be the reported fcab value.

FIG. 6 provides an enlarged view of the curve (401) from FIG. 4, representing where the same subject with the same base breath alcohol concentration (0.050 g/210 L) takes a fresh drink and blows into the same instrument (101). Note the elevated response to the initial pre-sample alcohol introduced during the blow (411), which results in a larger fcma result of 0.016 g/210 L. In this test, the actual alveolar sample, fcab, is elevated as well, and is measured at 0.120 g/210 L.

Because the ratio of fcma-to-fcab (thma) in the test in FIG. 5 is 0.02, and the thma in the test in FIG. 6 is 0.13, the valid and the mouth alcohol cases may be distinguished based on this ratio. Data from initial experiments has shown that a thma threshold of between about 0.05 and 0.07, preferably about 0.06 works well to separate valid samples from mouth alcohol samples, however, other thresholds may be used depending on the desired relative failure rates of either a false negative being provided (not detecting mouth alcohol when it is present) versus the likelihood of a false positive being produced (detecting mouth alcohol when it is not present). For the purposes of this disclosure, a thma of 0.06 will be used as the threshold. Since the thma of 0.02 from FIG. 5 is below 0.06, this threshold would declare the case in FIG. 5 a valid sample and report the fcab of 0.050 as the subject's valid, evidential reading. Conversely, since 0.13 is above 0.06, this threshold would declare the case in FIG. 6 an invalid sample due to mouth alcohol.

It follows that the exact thma threshold in use could vary depending on the exact hardware configuration in use. The threshold value could also be dependant on whether the alveolar sample lies in certain bracketed ranges, e.g., the thma threshold could be different depending on whether fcab is above or below 0.200 g/210 L. Or the thma threshold could be continuously variable by formula as fcab ranges from its maximum to minimum possible values. Alternatively, thma thresholds could be tied to fcma values instead of fcab values similar to dependencies described above.

The early sample introducing alcohol into the single fuel cell (103) is preferably small in relation to the size of the alveolar sample. This is because the recovery time needed by the fuel cell (103) between significant samples would generally prevent the proper analysis of the second, main sample. It is also to avoid contamination of the alveolar sample with the extra mouth alcohol. Generally therefore a small, controlled amount of breath is introduced into the fuel cell chamber prior to the main sample which is generally significantly larger.

An embodiment of this method would be utilizing the backpressure in the manifold (100) (when it exceeds the pressure inside the fuel cell) to force a small amount of breath (and in conjunction with continuous diffusion) through a very small hole in the fuel cell inlet port (104) onto the fuel cell itself. This inlet could be the same used for the alveolar sample, could be separate from the alveolar sample inlet, or could be a leak through the alveolar sample inlet when it is closed prior to the alveolar sample being taken. Another embodiment of this method would be to add a fuel cell exit port (105) so as to rely solely on flow generated by the manifold backpressure through the fuel cell (and not on diffusion into the cell.) Alternatively, if manifold backpressure is not sufficient, or doesn't even exist for some design reason such as no flow restriction (106), creating a vacuum at the fuel cell exit port (105) could be used to draw a sample through the fuel cell. In this case, even a volume-displacement device such as a continuous pump, could be attached to the exit port to draw a mouth alcohol sample through the fuel cell, as long as the total volume was on a much smaller scale than the alveolar sample. These inlet and exit ports in conjunction or separately, could be open all the time or open selectively via some control method such as a valve or check valve. Although it is generally preferred that mouth alcohol is sampled generally at a number of instants, or even continuously, up until the point of taking the alveolar sample, in other embodiments, this sampling and measurement may be terminated at any time prior to the taking of the alveolar sample or may comprise a single early sample. In an embodiment, the sample may also be an integrated sample measurement over time.

Figure 7:
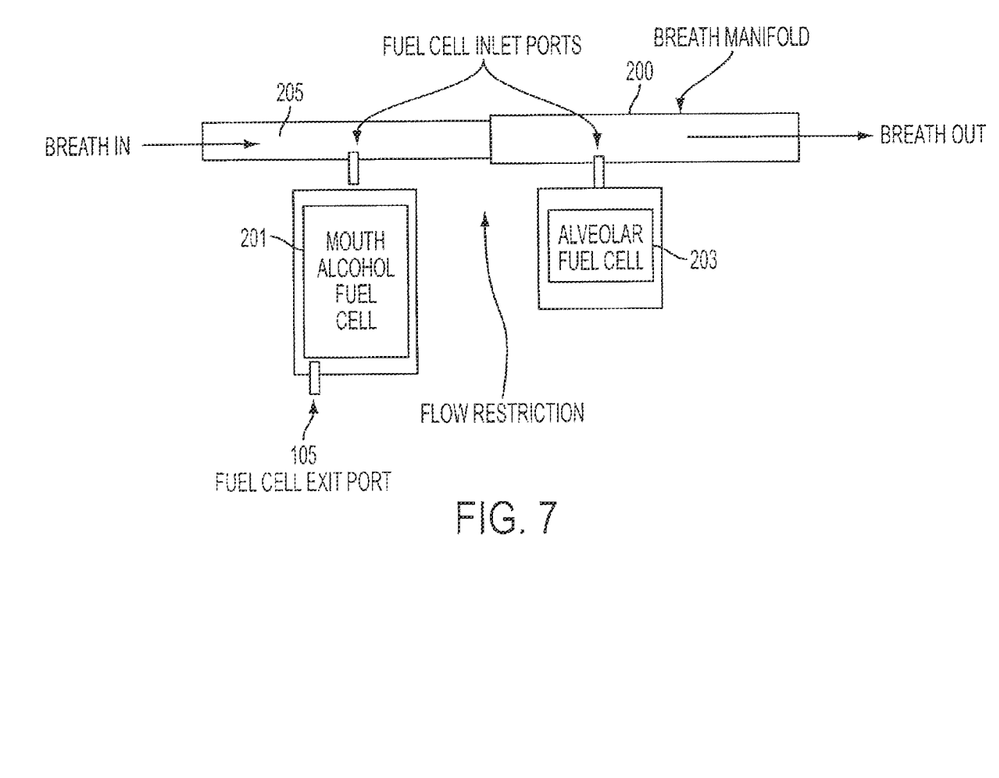
FIG. 7 shows a view of an embodiment of a dual fuel cell system.

In another embodiment, a similar system is used but it has two separate fuel cells. One such embodiment (200) is shown in FIG. 7. Even with two fuel cells, such a mouth alcohol detector (200) maintains a cost advantage over current infrared systems. The first cell (201) measures the alcohol concentration of a sample obtained early in the subject's blow, i.e., a first measuring sample, while the second (203) processes the standard end-of-blow alveolar sample, i.e., a second measuring sample. Although the implementation of this embodiment requires more mechanical and electronic complexity due to having to use the separate fuel cells (203) and (201), it mitigates possible interaction issues that may exist in the single cell embodiment (100) (shown in FIG. 3). A dual system such as this does not require that the mouth alcohol fuel cell be closest to the subject. There could easily be design reasons why the order of the two cells needs to be reversed. Alternatively, the breath flow could branch into two different paths, each leading to one of the two fuel cells.

Using the same concepts from the single cell system (100), described above, a method is present for the introduction of a mouth alcohol sample into the first cell (201). The amount of alcohol burned by the first, early sample mouth alcohol cell (201) during the blow may be measured in an embodiment and again labeled fcma. As with the single cell system, the calculation of fcma may or may not use the same method that will be employed to measure the alveolar sample; however, the fcma calculation will be a function of the signal returned from electronics (not shown) measuring the fuel cell (201) output.

From this point in the embodiment of the dual fuel cell system (200) a second alveolar sample is taken, using the same concepts for alveolar sampling described above for the single cell system, into the second fuel cell (203). This fuel cell is a replication of the prior art with no influence of the invention. The amount of alcohol burned in the cell (203) as a result of this discreet sample may then be measured and analyzed according to methods known in the art and may again be labeled; fcab. As with the single-cell embodiment, the ratio of the fcma-to-fcab values may be compared to a predetermined threshold, called thma. If the ratio exceeds this threshold, mouth alcohol is reported to the operator of the breath alcohol detection device and the alveolar sample declared invalid.

In a further embodiment of a dual fuel cell system (200), a first cell (201) may act exactly like a single fuel cell system (100), generating both the fcma and fcab results, but may be used for the sole purpose of determining the presence of mouth alcohol. The fcab result, in the mouth alcohol situation, however, would generally still not be useable when generated by either cell (201) and (203) even if that cell did not actually perform the mouth alcohol detection function. In such an embodiment, the second fuel cell (203) may be more specifically calibrated or designed to take an alveolar sample and report it as the subject reading in those cases where the first cell (201) found no mouth alcohol present. The first cell (201) can then also be specifically calibrated or designed to detect mouth alcohol as opposed to alveolar alcohol. This can also allow the second fuel cell (203) to eliminate any possible concern of residual breath samples in the first cell (201)

effecting the alveolar reading. In the mouth alcohol detection case, generally both fuel cell (201) and (203) fcab readings will be thrown out to reduce the possibility of inaccuracy returned by a mouth alcohol situation reading since an alveolar reading would still be elevated if mouth alcohol is present. However, this arrangement could provide for a more robust measuring scheme where each cell is specialized for a particular type of detection.

In a further embodiment of a dual fuel cell system (200), manifold pressure can be measured as an indication of flow, which can be used to calculate the volume of the subject's breath sample as the blow progresses as discussed above. This positive pressure is used to force the early sample into the mouth alcohol fuel cell (201). In an embodiment, a separate sampling mechanism (205) draws in the early sample into the fuel cell chamber (201). As the subject starts blowing, the flow and volume are measured, and after a small, early volume is seen, a sample, multiple samples, continuous samples, or sample integration can be drawn into the first fuel cell (201) for analysis. As the blow continues, and the volume measured is large enough to indicate deep lung, alveolar breath, a sample is then drawn into the second cell (203), where it is also analyzed.

In the embodiment shown in FIG. 7, back pressure is used to introduce a mouth alcohol sample into the cell (201) prior to the alveolar breath sample. Those skilled in the art will realize there are a variety of other possible ways to introduce this alcohol into the cell prior to the alveolar breath sample, such as diffusion, vacuum, pumping, and any other way known in the art.

In an embodiment, the algorithm disclosed herein used in detecting mouth alcohol can be generalized to be a function of all the data collected during the breath sample, which can be called $f(x1, x2, x3, \ldots)$. The result of this function can be compared to a threshold value, such as thma, and as before, the sample can be classified as mouth alcohol or non-mouth alcohol based on this comparison. The following function $f(\,)$ is one such embodiment:

$p_{ma}$=peak fuel cell signal seen from early, mouth alcohol sample, $r_{ab}$=alcohol result measured from the standard, alveolar breath sample, $t_{ab}$=time required for the fuel cell to burn the alveolar breath sample.

then:

$$f(p_{ma}, r_{ab}, t_{ab}) = p_{ma} * t_{ab}/r_{ab}$$

and:

thma=threshold of mouth alcohol hence:

$$f(p_{ma}, r_{ab}, t_{ab}) > \text{thma} \Rightarrow \text{mouth alcohol.}$$

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art. Accordingly, it is intended that all reasonably foreseeable addition, modifications, deletions and alterations be included within the scope of the invention as defined in the following claims.

The invention claimed is:

1. A breath alcohol tester, comprising:
    a breath manifold designed to accept breath from a human subject, said breath including an early breath followed by a later breath;
    a flow restriction, wherein an action of said breath in said breath manifold against said flow restriction creates a positive pressure in said breath manifold;
    a fuel cell; and
    a sampling system, the sampling system comprising an electrochemical volume-displacement device;
    wherein said manifold is configured to use said positive pressure in said manifold to force at least a portion of said early breath into said fuel cell via backpressure without said sampling system sampling said early breath;
    wherein the amount of alcohol forced into said fuel cell by said early breath is measured by said fuel cell as a first value;
    wherein at least a portion of said later breath is displaced by said sampling system and provided to said fuel cell;
    wherein the amount of alcohol in the portion at said later breath displaced by said sampling system is measured by said fuel cell as a second value; and
    wherein if a ratio of said first value to said second value is above a predetermined threshold said breath alcohol tester disregards said second value.

2. The tester of claim 1 wherein said portion of said early breath has a smaller volume than said sample of said later breath.

3. The tester of claim 1 wherein said threshold is between about 0.05 and 0.07.

4. The tester of claim 3 wherein said threshold is about 0.06.

5. The tester of claim 1 wherein said tester includes a second fuel cell and a second sampling system, said second fuel cell also taking in a sample of said later breath from said sampling system.

6. The tester of claim 5 wherein if said ratio is below said predetermined value said second fuel cell measures the human subject's breath alcohol level.

7. The tester of claim 5 wherein said later breath comprises alveolar breath.

8. The tester of claim 1 wherein said later breath comprises alveolar breath.

9. The tester of claim 1 wherein pressure within said breath manifold is used to distinguish said early breath from said later breath.

10. A breath alcohol tester, comprising:
    a breath manifold;
    a flow restriction;
    a sampling system, the sampling system comprising an electrochemical volume-displacement device;
    a first fuel cell; and
    a second fuel cell;
    wherein said breath manifold is designed to accept breath from a human subject, said breath including an early breath followed by a later breath;
    wherein the action of said breath in said breath manifold against said flow restriction creates a positive pressure in said breath manifold;
    wherein said manifold is configured to use said positive pressure forces at least a portion of said early breath into said first fuel cell without said sampling system sampling said early breath;
    wherein the amount of alcohol in said early breath is calculated by said first fuel cell as a first value;

wherein at least a portion of said later breath is displaced by said sampling system and provided to said second fuel cell;

wherein the amount of alcohol in said later breath is calculated by said second fuel cell as a second value;

wherein the ratio of said first value to said second value is determined and compared to a predetermined threshold; and wherein if said ratio exceeds said threshold, said breath alcohol tester indicates the presence of mouth alcohol.

11. The tester of claim 10 wherein said portion of said early breath has a smaller volume than said portion of said later breath.

12. The tester of claim 10 wherein said threshold is between about 0.05 and 0.07.

13. The tester of claim 12 wherein said threshold is about 0.06.

14. The tester of claim 10 wherein said later breath comprises alveolar breath.

15. The tester of claim 10 wherein pressure within said breath manifold is used to distinguish said early breath from said later breath.

16. The tester of claim 15 wherein said pressure is used to monitor flow of breath.

* * * * *